(12) United States Patent
Lowery

(10) Patent No.: US 6,245,088 B1
(45) Date of Patent: Jun. 12, 2001

(54) RETRIEVABLE UMBRELLA SIEVE AND METHOD OF USE

(76) Inventor: Samuel R. Lowery, 400 N. Main St. Apt. 7, Fostoria, OH (US) 44830

( * ) Notice: Subject to any disclaimer, the term of this patent is extended or adjusted under 35 U.S.C. 154(b) by 0 days.

(21) Appl. No.: 09/374,833

(22) Filed: Aug. 14, 1999

Related U.S. Application Data

(63) Continuation of application No. 09/110,764, filed on Jul. 3, 1998.
(60) Provisional application No. 60/051,774, filed on Jul. 7, 1997.

(51) Int. Cl.[7] .................................................. A61B 17/00
(52) U.S. Cl. ............................................................ 606/200
(58) Field of Search .................................. 606/200, 194, 606/198, 192, 108; 604/96, 104–108

(56) References Cited

U.S. PATENT DOCUMENTS

| 5,769,816 | 6/1998 | Barbut et al. . |
| 5,814,064 | 9/1998 | Daniel et al. . |
| 6,007,557 | * 12/1999 | Ambrisco et al. .................... 606/200 |

* cited by examiner

*Primary Examiner*—Michael Buiz
*Assistant Examiner*—Hoa B. Trinh
(74) *Attorney, Agent, or Firm*—John J. Elnitski, Jr.

(57) ABSTRACT

The present invention is a retrievable umbrella sieve for removing blood clots and other debris in blood vessels. The umbrella sieve also functions to prevent blood clots and other derbies from reaching the heart of a human or animal. One of the main uses of the umbrella sieve is for the insertion of the Inferior Vena Cava to prevent and remove blot clots before the clots reach the heart. There are two embodiments of the umbrella sieve. The umbrella sieve provides a method and apparatus for used during the medical surgical treatment phase of thrombophlebitis and venous thrombosos in the precautionary prevention of pulmonary emboli. The umbrella sieve provides a method and apparatus for routinely placing a preventive device in lower extremity fractures, especially that of the hip, in anticipation of preventing pulmonary emboli. The umbrella sieve provides a method and apparatus that is retrievable.

22 Claims, 7 Drawing Sheets

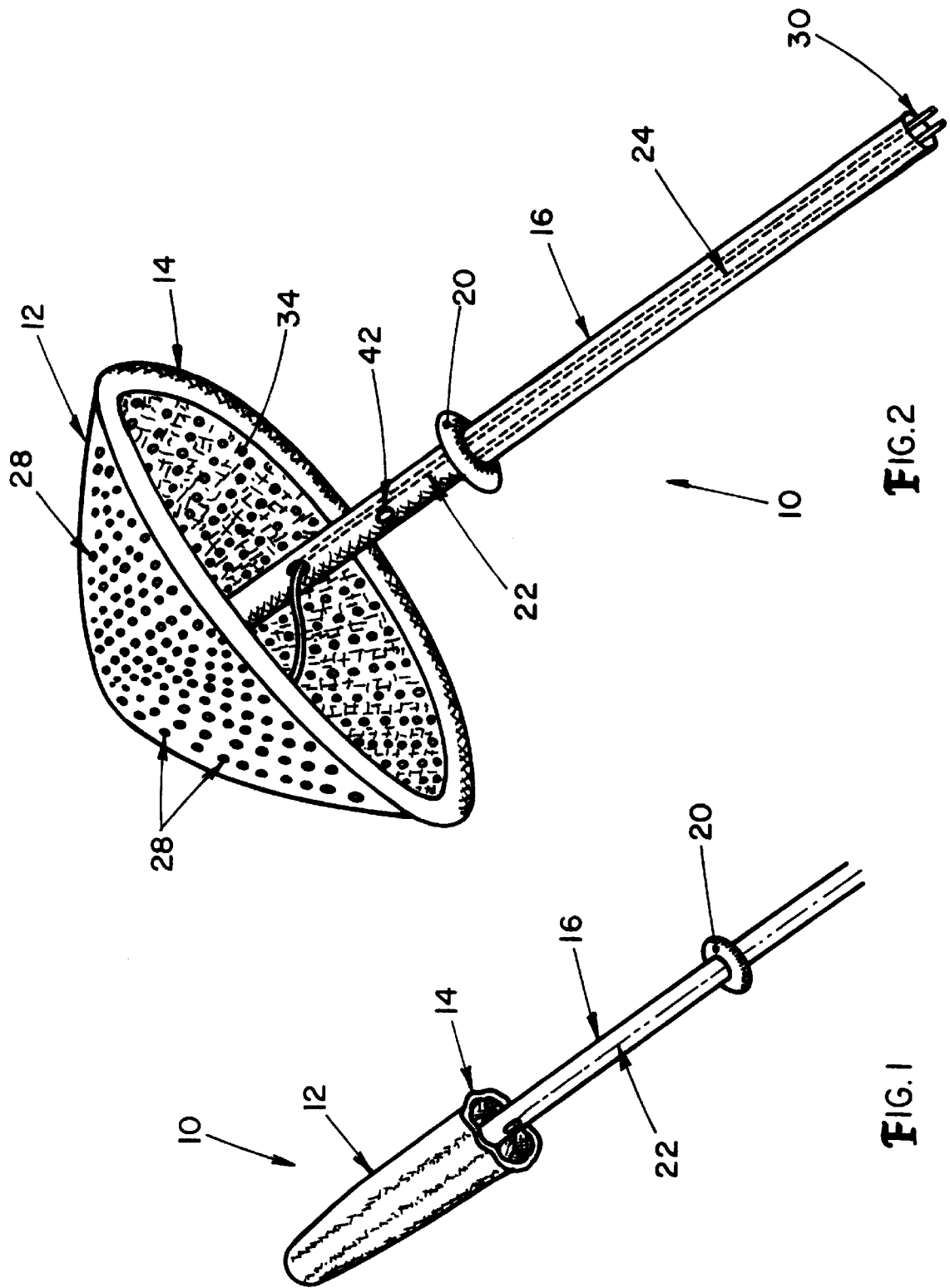

RETRIEVABLE UMBRELLA SIEVE AND METHOD OF USE

This CPA application claims priority to U.S. Provisional Application No. 60/051,774 filed Jul. 7, 1997 and this application is a continuation of U.S. patent application Ser. No. 09/110,764 filed Jul. 3, 1998, which are herein incorporated by reference.

BACKGROUND

The medical community is in constant search for new ways to prevent blood clots from reaching the heart of humans and animals, as well as other objects or debris in the blood flow which may cause health problems. It is an object of the present invention to provide a method and apparatus for catching any blood clots, or other debris, that might dislodge from their origin of the veins in the pelvic or femoral systems. Another object of the present invention is to provide a method and apparatus for used during the medical surgical treatment phase of thrombophlebitis and venous thrombosos in the precautionary prevention of pulmonary emboli. Another object of the present invention is to provide a method and apparatus for routinely placing a preventive device in lower extremity fractures, especially that of the hip, in anticipation of preventing pulmonary emboli. Another object of the present invention is to provide a method and apparatus for a non-permanent manner of accomplishing the foregoing, whereby the apparatus is retrievable.

SUMMARY OF THE INVENTION

The present invention is an umbrella sieve for capturing objects in a blood vessel which includes an inserter tube having a top; an umbrella cap having a lower peripheral circumference edge and an ability to fold like a rain umbrella; the umbrella cap having a perforated surface to allow the passage of fluids of the blood vessel; the umbrella cap being attached to the top of the inserter tube; an inflatable circumfrential balloon attached to the lower peripheral circumference edge for extending the umbrella cap when inflated; a first inflation line connected to the circumfrential balloon for inflating the circumfrential balloon. The umbrella sieve also includes an occlusive membrane attached to the inserter tube and below the umbrella cap; and wherein the membrane is extendible around the inserter tube to form a treatment compartment. The method of using the umbrella sieve includes inserting the umbrella sieve into the blood vessel; inflating the circumfrential balloon to extend the umbrella cap; capturing objects in flow of the blood vessel; removing any objects captured; deflating the circumfrential balloon; and removing the umbrella sieve. The method also includes extending the membrane around the inserter tube to form a treatment compartment by inflating the occlusive balloon attached to the membrane from a second inflation line after capturing of the objects to form a treatment compartment and further including before removal of the umbrella sieve, the deflation of the occlusive balloon to retract the occlusive membrane.

BRIEF DESCRIPTION OF THE DRAWINGS

FIG. 1 is a perspective view of an umbrella sieve in an uninflated state according to the present invention;

FIG. 2 is a perspective view of the umbrella sieve with an inflated circumfrential balloon and an umbrella cap extended according to the present invention;

DETAILED DESCRIPTION

Figure 3:
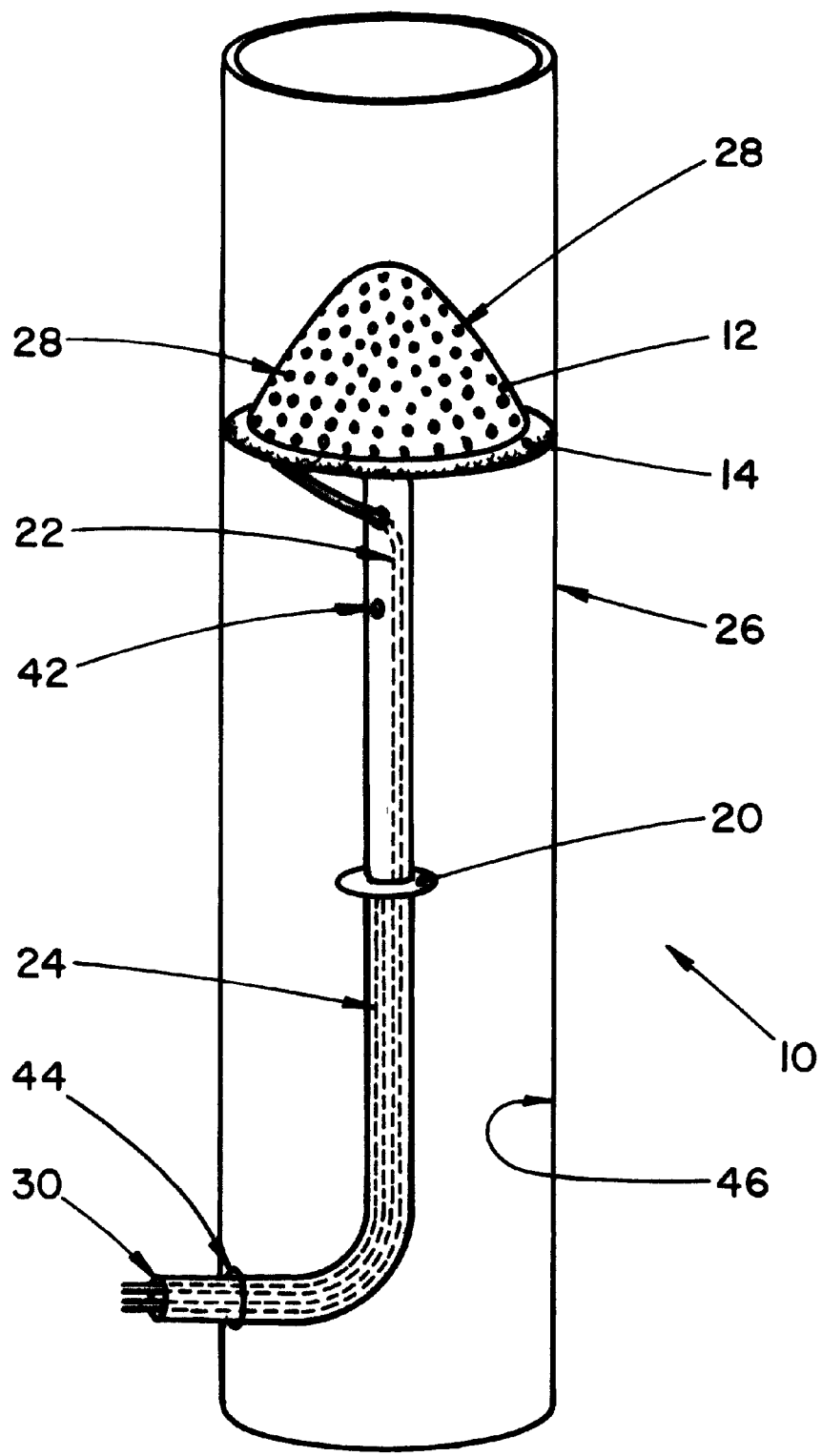
FIG. 3 is a perspective view of the umbrella sieve inserted into an Inferior Vena Cava with the umbrella cap fully extended according to the present invention.

The present invention is a retrievable umbrella sieve for removing blood clots and other debris in blood vessels. The umbrella sieve also functions to prevent blood clots and other derbies from reaching the heart of a human or animal. One of the main uses of the umbrella sieve is for the insertion of the Inferior Vena Cava to capture and remove blot clots before the clots reach the heart. FIGS. 1–5 show the components of the umbrella sieve 10. FIGS. 1–4 show a first embodiment and FIG. 5 shows a second embodiment of the umbrella sieve 10.

The main components of the umbrella sieve 10 are an umbrella cap 12, circumfrential balloon 14, inserter tube 16, occlusive membrane 18, occlusive balloon 20, first inflation line 22 and a second inflation line 24. FIG. 1 shows the umbrella sieve 10 in an uninflated state and ready for insertion into the Inferior Vena Cava 26. As shown in FIGS. 2–5, the umbrella cap 12 includes perforations 28 to allow blood or other fluids to flow through the umbrella cap 12, while catching blood clots or other debris. The material for the umbrella cap 12 is preferably a thin flexible Teflon, but could be of any material that allows opening and closing similar to a rain umbrella. The inserter tube 16 is a tube to aid insertion of the umbrella cap 12 and can be flexible in nature. The inserter tube 16 is show in FIGS. 1–4 as a hollow tube 30 and shown in FIG. 5 as a solid tube 32. Either embodiment of the tubes 30, 32 can be made of nylon or Teflon. The inserter tube 16 is attached at the top center of an inside surface 34 of the cap 12. The inserter tube 16 is attached using any surgically safe glue or other surgically compatible method of attachment. The circumfrential balloon 14 is attached around a lower peripheral circumference edge 36 of the umbrella cap 12. FIG. 1 shows the circumfrential balloon 14 uninflated and FIGS. 2–5 show the circumfrential balloon 12 inflated. Attachment of the circumfrential balloon 14 to the cap 12 is with a surgically safe glue or other surgically compatible method of attachment.

The occlusive balloon 20 is mounted to the inserter tube 12 below the uninflated circumfrential balloon 14. The occlusive balloon 20 includes a solid elastic occlusive membrane 18 shown in FIG. 4, which extends outward from the inserter tube 16 when the occlusive balloon 20 is inflated. The occlusive membrane 18 can be part of the occlusive balloon 20 or a separate membrane attached between the inserter tube 16 and the occlusive balloon 2. In either case, the inside circumference of the occlusive membrane 18 would be attached to the inserter tube 16 using surgically safe glue or other surgically compatible method of attaching the membrane 18. The first and second inflation lines 22, 24 are mounted inside the hollow tube 30 of the first embodiment as shown in FIGS. 1–4 and outside the solid tube 32 of the second embodiment as shown in FIG. 5. For the first embodiment, the inserter tube 16 includes inflation line openings 40 to route the inflation lines 22, 24 from the inside of the inserter tube 16 to the outside of the inserter tube 16 and on to the balloons 14, 20. For the second embodiment, the inflation lines 22, 24 are attached to the outside of the solid tube 32 using any surgically safe glue or other surgically compatible method of attachment. The first inflation line 22 supplies an inflation fluid to the circumfrential balloon 14 and the second inflation line 24 supplies an inflation fluid to the occlusive balloon 20. The inflation fluid is used to inflate balloons 14, 20 and can be of any surgically safe fluid, such as air or saline solution. The first embodiment also includes a instrument opening 42 to permit the insertion of scopes and other devices into the area under the umbrella cap 12.

FIG. 1 shows the umbrella sieve 10 prepared for insertion, where both balloons are uninflated and the umbrella cap 12 is folded down like a rain umbrella. FIG. 2 shows the umbrella sieve 10 with the umbrella cap 12 extended due to inflation of circumfrential balloon 14. The umbrella sieve 10 is inserted into the Inferior Vena Cava 26 in the uninflated state of FIG. 1, using standard medical procedures. After insertion into the Inferior Vena Cava 26, FIG. 3 shows the umbrella sieve 10 with the circumfrential balloon 14 inflated by the inflation fluid, which opens the umbrella cap 12. When the circumfrential balloon 14 is fully inflated as shown in FIG. 3, the balloon 14 impinges on the tunica 46 of the Vena Cava 26 and creates a seal. At this point the umbrella cap 12 with its perforations 28 allows the blood to flow through the Vena Cava 26, but will prohibit further travel of any dislodged blood clots or other debris through the blood stream. This affords the opportunity for clearing by surgical or enzymatic techniques.

Figure 4:
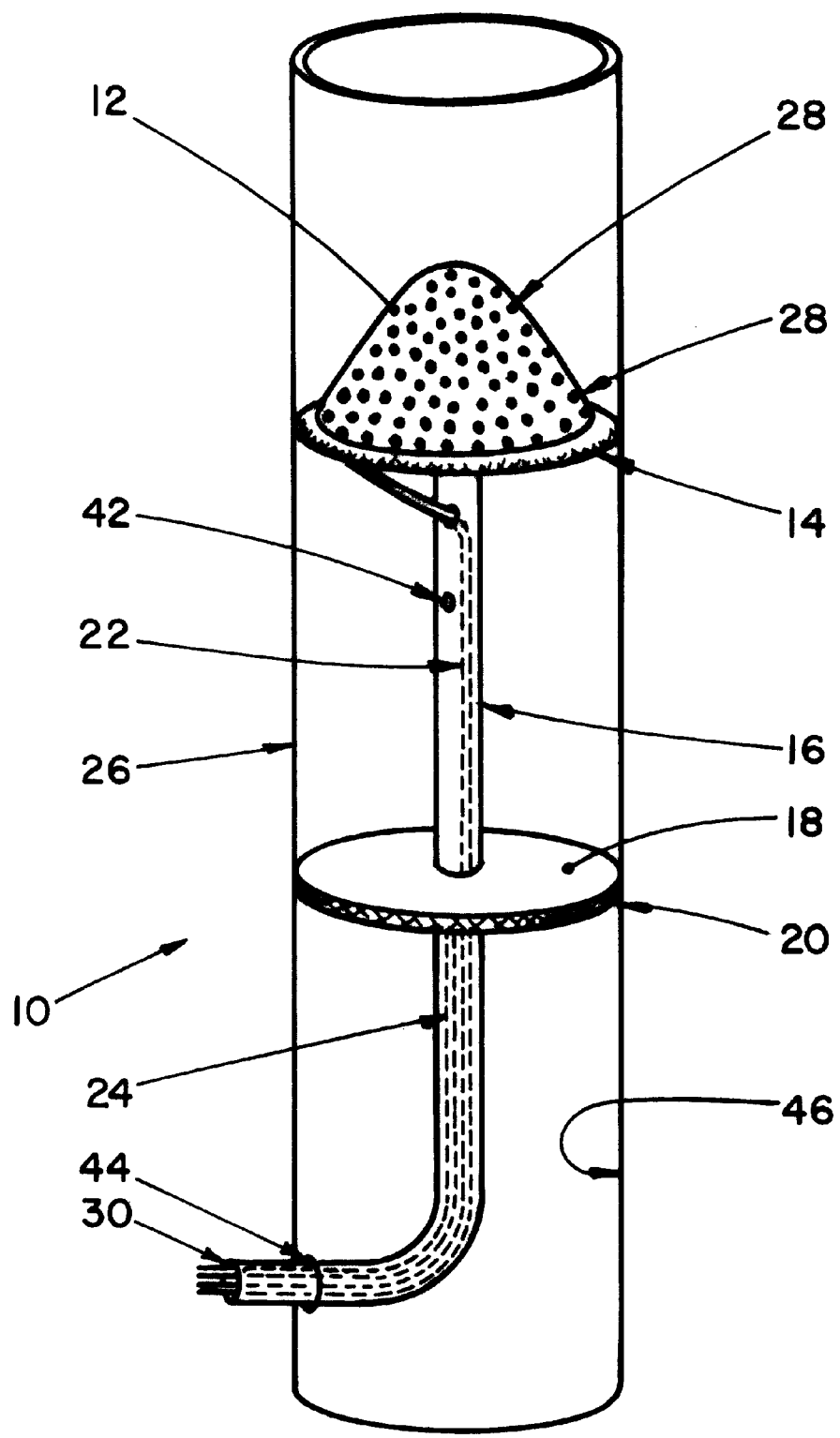
FIG. 4 is a perspective view of the umbrella sieve inserted into the Inferior Vena Cava with the umbrella cap fully extended and an occlusive membrane fully extended according to the present invention.
Figure 5:
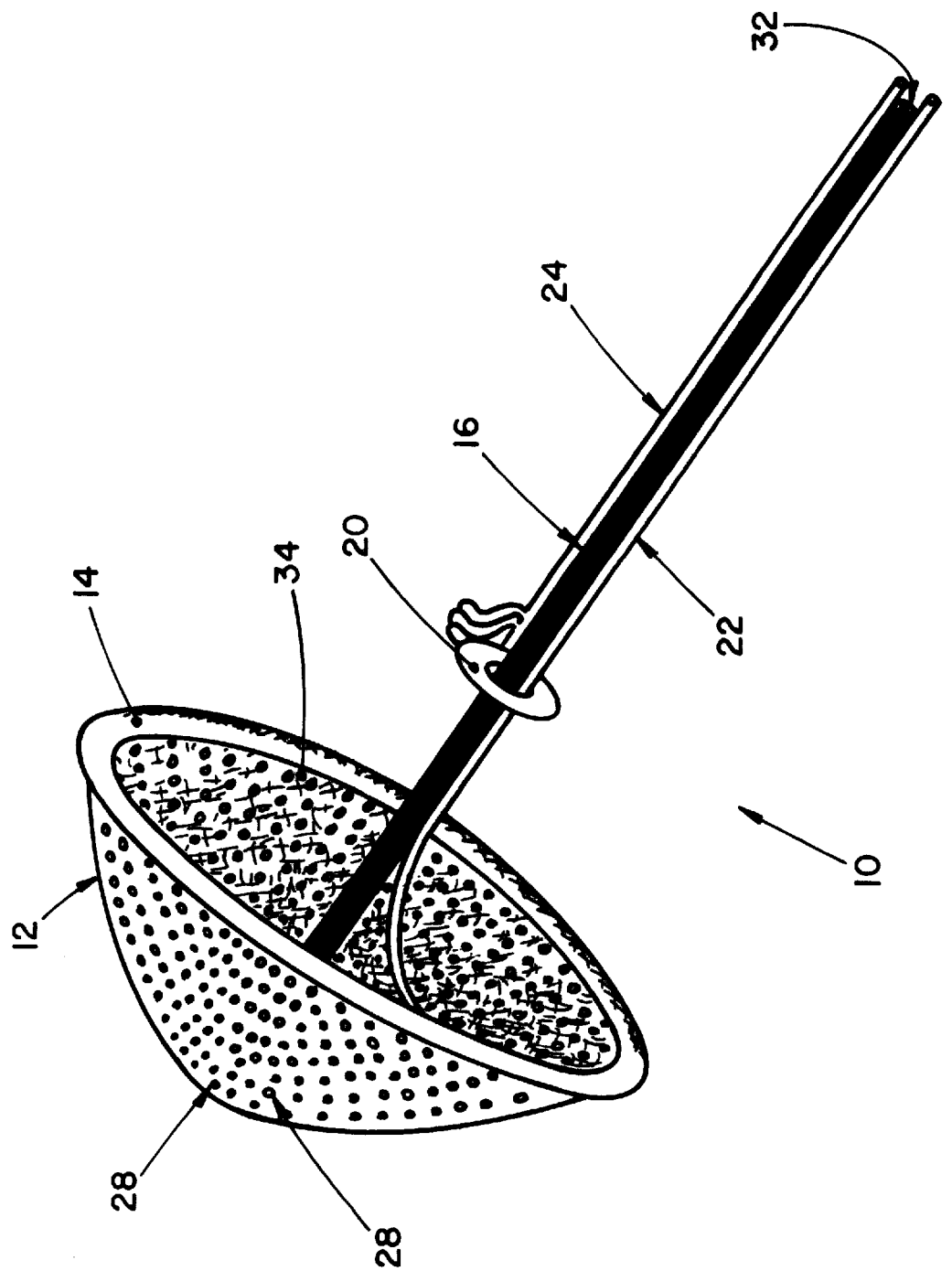
FIG. 5 is a perspective view of the umbrella sieve of a second embodiment according to the present invention.

FIG. 4 shows the umbrella sieve 10 inserted into the Inferior Vena Cava 26 as illustrated in FIG. 3, but with the occlusive balloon 20 inflated. When the occlusive balloon 20 is fully inflated, the balloon 20 impinges upon the tunica 46 of the Vena Cava 26. The tunica 46 is the inside surface of the Vena Cava 26. The full inflation of the occlusive balloon 20 produces a treatment compartment 48 between the inside surface 34 of the umbrella cap 12 and the occlusive membrane 18. Once blood clots or other debris are captured and identified in the area of the umbrella cap 12, the occlusive balloon 20 is inflated by the second inflation line 24 with the fluid. Once the treatment compartment 48 is established, any trapped objects can be suctioned out and the treatment compartment 48 irrigated with normal saline. After removal of the objects, the treatment compartment 48 can be examined for the presence of further clots and/or debris by the use of fiber optics scopes inserted through the instrument opening 42 for the first embodiment or by other means of using scopes for the second embodiment.

Figure 6:
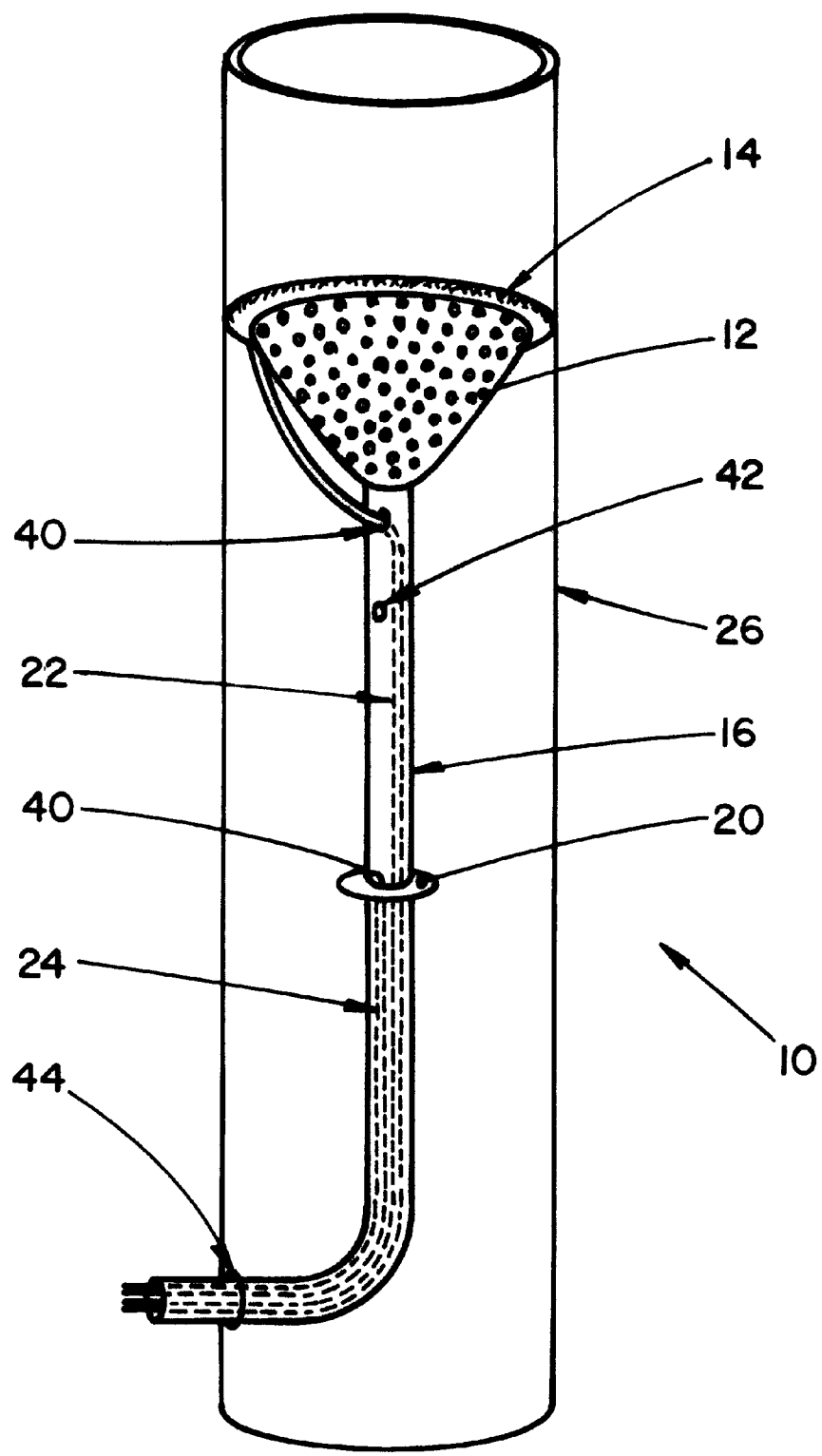
FIG. 6 is a perspective view of the umbrella sieve with the umbrella cap partially inverted in preparation of retrieval of the umbrella sieve according to the present invention.
Figure 7:
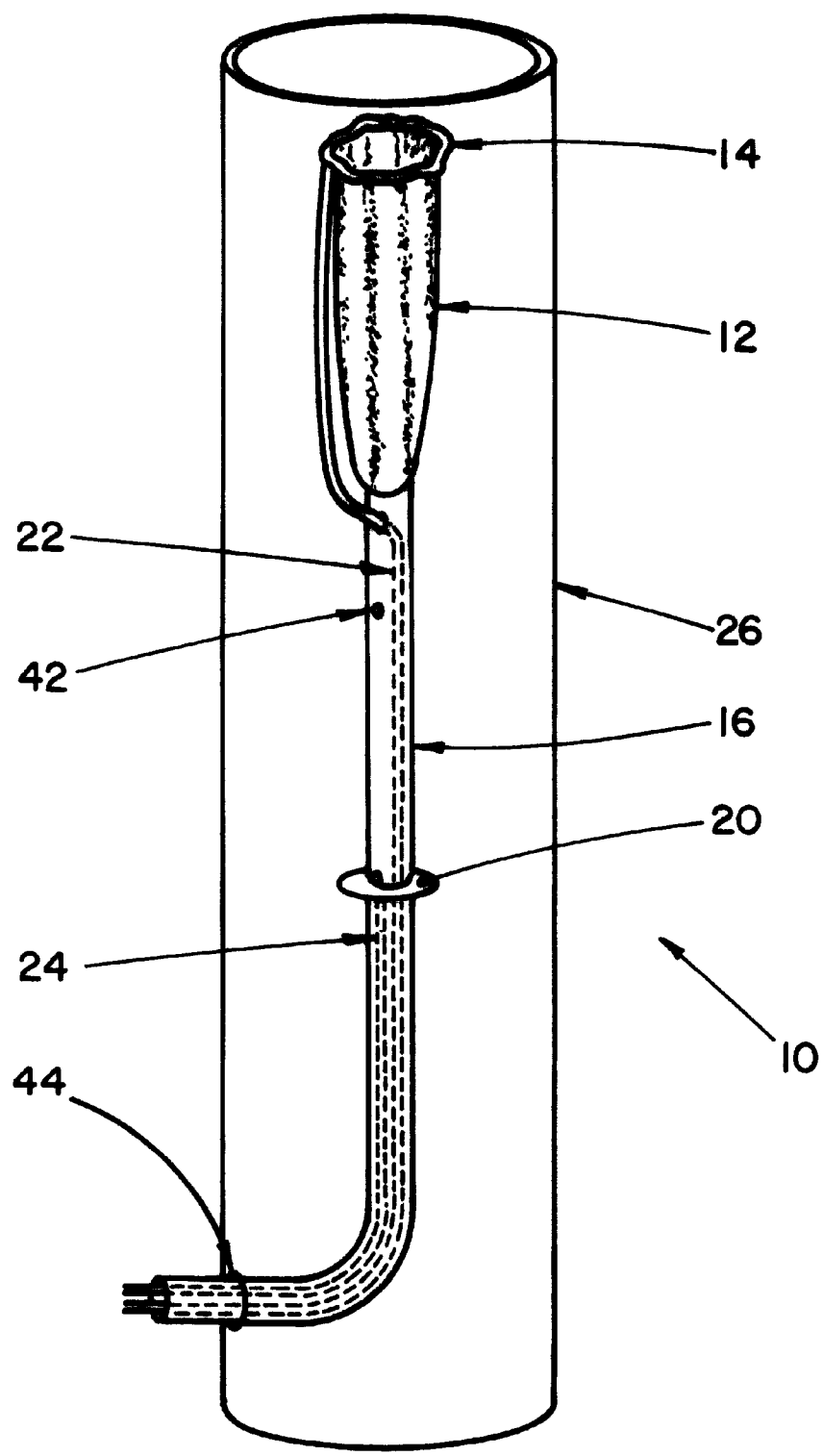
FIG. 7 is a perspective view of the umbrella sieve with the umbrella cap fully inverted during retrieval of the umbrella sieve according to the present invention.

After treatment, the occlusive balloon 20 is deflated to resume normal blood flow through the Vena Cava 26. Upon decision that the umbrella sieve 10 is no longer required, the circumfrential balloon 14 is deflated and the entire umbrella sieve 10 is retrieved from the Vena Cava 26. The umbrella cap 12 is flexible enough so that the as the umbrella sieve 10 is retrieved, the cap 12 inverts and folds down like a reversed rain umbrella in the wind, as shown in FIGS. 6 and 7.

Figure 8:
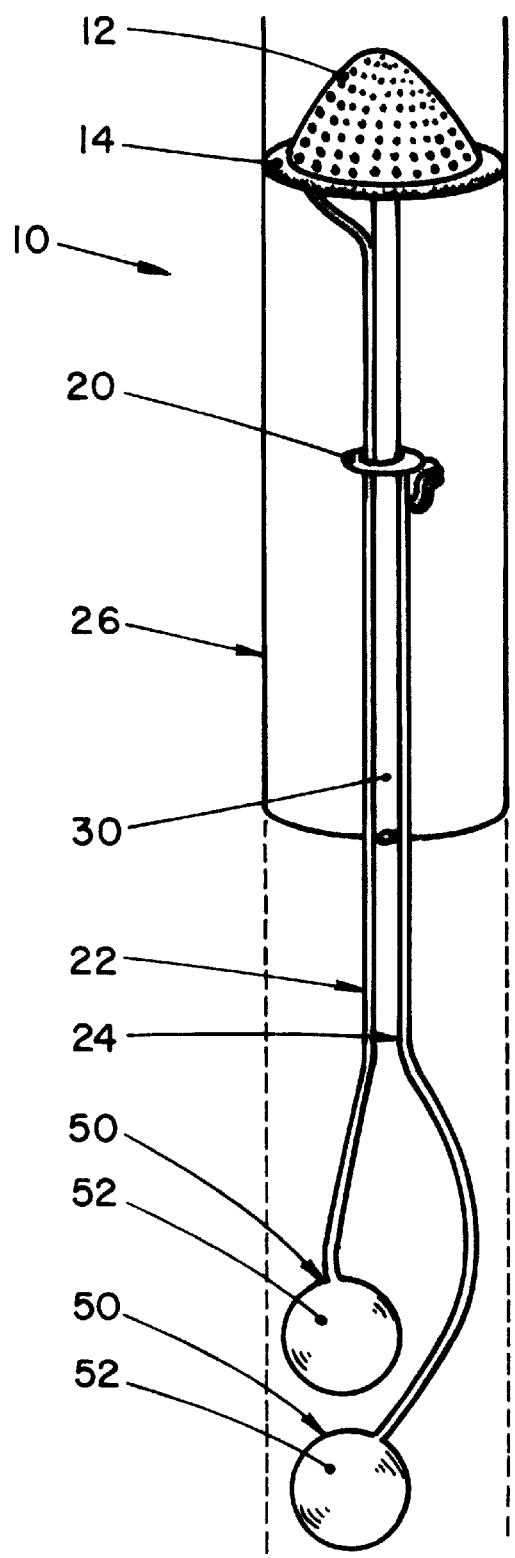
FIG. 8 is a perspective view of an umbrella sieve in an uninflated state having a hollow inserter tube and including inflation reservoirs according to the present invention.
Figure 9:
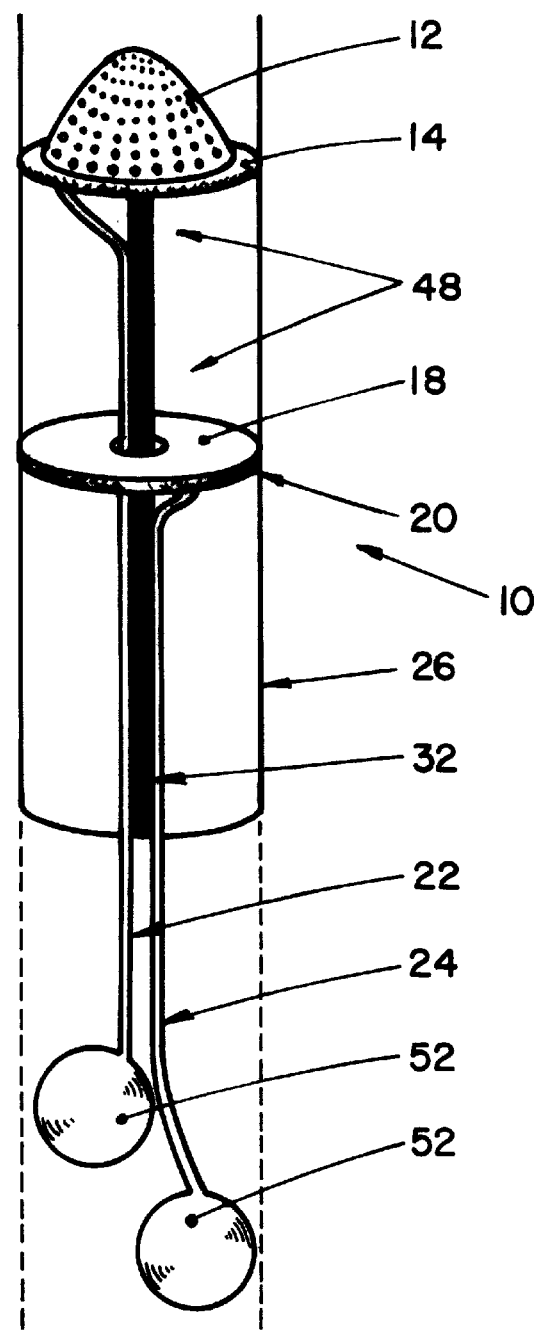
FIG. 9 is a perspective view of an umbrella sieve in an uninflated state having a solid inserter tube and including inflation reservoirs according to the present invention.

FIGS. 8 and 9 show the addition of two inflation reservoirs 50 cemented to the first and second inflation lines 22, 24. Each inflation reservoir 50 contains a sterilized fluid 52 such as air or radiopaque saline to inflate the circumfrential balloon 14 and the occlusive balloon 20. Use of the sterilized fluid 52 aids in preventing infection as does the use of the inflation reservoirs 50. The inflation reservoirs 50 are flexible so that the sterilized fluid can be force into the first and second inflation lines 22, 24. The inflation reservoirs 50 are implanted in groin tissue just below the inguinal ligament. To inflate either the circumfrential balloon 14 or the occlusive balloon 20, pressure is applied on the skin overlying the appropriate inflation reservoir 50 to inflate desired balloon due to the movement of the sterilized fluid. To deflate either the circumfrential balloon 14 or the occlusive balloon 20, simply release the pressure on the appropriate inflation reservoir 50 and the sterilized fluid returns to the inflation reservoir 50. Either the circumfrential balloon 14 or the occlusive balloon 20 may remained inflated using the inflation reservoirs 50 by keeping pressure on the inflation reservoirs 50 using some type of pressure wrap (not shown) about that area of the skin where the inflation reservoirs 50 are located. The inflation reservoirs 50 are about one-half the size of a standard golf ball. The addition of the inflation reservoirs 50 to the system, allows ready activation of the treatment compartment 48 at any chosen time with the use of thumb pressure on the skin overlying the reservoir 50. The circumfrential balloon 14 is usually inflated at the time of insertion. The circumfrential balloon 14 can be periodically inflated and deflated several times to discourage or inhibit overgrowth of tunica intima.

The present invention therefore provides a method and apparatus for catching any blood clots, or other debris, that might dislodge from their origin of the veins in the pelvic or femoral systems. It provides a method and apparatus for used during the medical surgical treatment phase of thrombophlebitis and venous thrombosos in the precautionary prevention of pulmonary emboli. It provides a method and apparatus for routinely placing a preventive device in lower extremity fractures, especially that of the hip, in anticipation of preventing pulmonary emboli. It provides a method and apparatus for a non-permanent manner of accomplishing the foregoing, whereby the apparatus is retrievable. It provides a treatment compartment for trapping and removal of clots or debris. It provides a method and apparatus usable during the course of treatment for dependent venous thrombosis, with the umbrella sieve in place, should there develop clinical evidence of increasing Vena Caval pressure. It can be used for the prevention of chronic progressive dependent edema.

While embodiments of the invention have been described in detail herein, it will be appreciated by those skilled in the art that various modifications and alternatives to the embodiments could be developed in light of the overall teachings of the disclosure. Accordingly, the particular arrangements are illustrative only and are not limiting as to the scope of the invention which is to be given the full breadth of the appended claims and any and all equivalents thereof.

I claim:

1. An umbrella sieve for capturing objects in a blood vessel comprising:

an inserter tube being a hollow tube and having a top and inflation line opening;

an umbrella cap having a lower peripheral circumference edge and an ability to fold like a rain umbrella;

said umbrella cap having a perforated surface to allow the passage of fluids of the blood vessel;

said umbrella cap attached to said top of said inserter tube; and an inflatable circumfrential balloon attached to said lower peripheral circumference edge for extending said umbrella cap when inflated;

a first inflation line connected to said circumfrential balloon for inflating said circumfrential balloon, said first inflation line running along an inside of said hollow tube and exiting out said inflation line opening.

2. The umbrella sieve of claim 1, wherein said inserter tube is flexible.

3. An umbrella sieve for capturing objects in a blood vessel comprising:

an inserter tube having a top;

an umbrella cap having a lower peripheral circumference edge and an ability to fold like a rain umbrella;

said umbrella cap having a perforated surface to allow the passage of fluids of the blood vessel;

said umbrella cap attached to said top of said inserter tube;

an inflatable circumfrential balloon attached to said lower peripheral circumference edge for extending said umbrella cap when inflated;

a first inflation line connected to said circumfrential balloon for inflating said circumfrential balloon; and an occlusive membrane attached to said inserter tube and below said umbrella cap; and wherein said membrane is extendible from around said inserter tube toward an inside wall of the blood vessel in order to form a treatment compartment.

4. The umbrella sieve of claim 3, further including an inflatable occlusive balloon attached to said occlusive membrane for extending said occlusive membrane and further including a second inflation line for inflating said occlusive balloon.

5. The umbrella sieve of claim 4, wherein said inserter tube is hollow and includes an inflation line opening for the exiting of said second inflation line which runs along an inside of said hollow tube and exits out said inflation line opening.

6. The umbrella sieve of claim 4, wherein said inserter tube is a solid flexible tube and said first and second inflation lines are mounted to an outside surface of said inserter tube.

7. An umbrella sieve for capturing objects in a blood vessel comprising:

an inserter tube having a top;

an umbrella cap having a lower peripheral circumference edge, said umbrella cap being foldable like a rain umbrella and also being foldable in a reverse direction of normal for a rain umbrella to allow retrieval of said umbrella sieve;

said umbrella cap having a perforated surface to allow the passage of fluids of the blood vessel;

said umbrella cap attached to said top of said inserter tube;

an inflatable circumfrential balloon attached to said lower peripheral circumference edge for extending said umbrella cap when inflated; and a first inflation line connected to said circumfrential balloon for inflating said circumfrential balloon.

8. An umbrella sieve for capturing objects in a blood vessel comprising:

an inserter tube having a top;

an umbrella cap having a lower peripheral circumference edge and an ability to fold like a rain umbrella;

said umbrella cap having a perforated surface to allow the passage of fluids of the blood vessel;

said umbrella cap attached to said top of said inserter tube;

an inflatable circumfrential balloon attached to said lower peripheral circumference edge for extending said umbrella cap when inflated;

a first inflation line connected to said circumfrential balloon for inflating said circumfrential balloon; and an inflation reservoir attached to said first inflation line, said inflation reservoir being flexible and capable of containing a sterilized fluid used to inflate said circumfrential balloon.

9. The umbrella sieve of claim 8, wherein said inserter tube is a hollow tube.

10. The umbrella sieve of claim 9, wherein said first inflation line runs along inside said hollow tube and exits out an inflation line opening.

11. The umbrella sieve of claim 8, wherein said inserter tube is a solid tube.

12. The umbrella sieve of claim 11, wherein said first inflation line is attached to an outside surface of said inserter tube.

13. The umbrella sieve of claim 8, future including an occlusive membrane attached to said inserter tube and below said umbrella cap; and wherein said membrane is extendible outward from around said inserter tube to an inside wall of the blood vessel in order to form a treatment compartment.

14. The umbrella sieve of claim 13, further including an inflatable occlusive balloon attached to said occlusive membrane for extending said occlusive membrane and further including a second inflation line for inflating said occlusive balloon.

15. The umbrella sieve of claim 14, wherein said inserter tube is hollow and includes an inflation line opening for the exiting of said second inflation line which runs along inside said hollow tube and exits out said inflation line opening.

16. The umbrella sieve of claim 14, wherein said inserter tube is a solid flexible tube and said second inflation line is mounted to an outside surface of said inserter tube.

17. The umbrella sieve of claim 8, wherein said umbrella cap folds in a reverse direction for retrieval of said umbrella sieve.

18. A method of capturing and removing objects in a blood vessel using an umbrella sieve that includes an inserter tube having a top; an umbrella cap having a lower peripheral circumference edge and ability to fold like a rain umbrella; the umbrella cap having a perforated surface to allow the passage of fluids; the umbrella cap attached to the top of the inserter tube; an inflatable circumfrential balloon attached to the lower peripheral circumference edge for extending the umbrella cap when inflated; a first inflation line connected to the circumfrential balloon for inflating the circumfrential balloon; and an occlusive membrane attached to the inserter tube and below the umbrella cap, wherein the occlusive membrane is extendible outward from around the inserter tube toward an inside wall of the blood vessel in order to form a treatment compartment; comprising:

inserting the umbrella sieve into the blood vessel;

inflating the circumfrential balloon to extend the umbrella cap;

capturing objects in flow of the blood vessel;

removing the objects captured;

extending said occlusive membrane when desired to form said treatment compartment;

deflating the circumfrential balloon when desired to allow the objects to enter the treatment compartment; and deflating the circumfrential balloon and the retracting the occlusive membrane when desired to removing the umbrella sieve.

19. The method of claim 18, further including an occlusive balloon attached to said occlusive membrane; further including a second inflation line connected to said occlusive balloon; and wherein the occlusive membrane is extendible outward from the inserter tube to form said treatment compartment by inflating the occlusive balloon; and further including before removal of the umbrella sieve, the deflation of the occlusive balloon to retract the occlusive membrane.

20. A method of capturing and removing objects in a blood vessel using an umbrella sieve that includes an inserter tube having a top; an umbrella cap having a lower peripheral circumference edge and ability to fold like a rain umbrella; the umbrella cap having a perforated surface to allow the passage of fluids; the umbrella cap attached to the top of the inserter tube; an inflatable circumfrential balloon attached to the lower peripheral circumference edge for extending the umbrella cap when inflated; a first inflation line connected to the circumfrential balloon for inflating the circumfrential balloon; and a first inflation reservoir attached to the first inflation line, the inflation reservoir being flexible and capable of containing a sterilized fluid used to inflate said circumfrential balloon; comprising:

inserting the umbrella sieve into the blood vessel;

inflating the circumfrential balloon to extend the umbrella cap by applying pressure to the first inflation reservoir attached to the first inflation line;

capturing objects in flow of the blood vessel;

removing the objects captured;

deflating the circumfrential balloon when desired by removing the pressure to the first inflation reservoir attached to the first inflation line; and removing the umbrella sieve.

21. The method of claim 20, further including an occlusive membrane attached to said inserter tube and below said umbrella cap, wherein said membrane is extendible outward from around said inserter tube to an inside wall of the blood vessel in order to form a treatment compartment.

22. The method of claim 21, further including an occlusive balloon attached to the occlusive membrane; further including a second inflation line attached to the occlusive balloon; further including a second inflation reservoir attached to said second inflation line, said second inflation reservoir being flexible and capable of containing a sterilized fluid used to inflate said occlusive balloon; wherein said membrane is extendible outward from around said inserter tube by applying pressure to the second inflation reservoir attached to the first inflation line; and wherein the occlusive balloon is deflated by removing the pressure to the second inflation reservoir attached to the second inflation line.

* * * * *